United States Patent
Naijo et al.

(10) Patent No.: US 6,316,563 B2
(45) Date of Patent: *Nov. 13, 2001

(54) THERMOPOLYMERIZABLE COMPOSITION AND USE THEREOF

(75) Inventors: Shuichi Naijo; Koji Tokita; Masataka Takeuchi, all of Chiba (JP)

(73) Assignee: Showa Denko K.K., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,598

(22) Filed: May 27, 1998

Related U.S. Application Data

(60) Provisional application No. 60/064,731, filed on Nov. 6, 1997.

(30) Foreign Application Priority Data

May 27, 1997 (JP) .................................... 9-136947
Sep. 10, 1997 (JP) .................................... 9-245613

(51) Int. Cl.$^7$ ............................ C08F 4/32; C08F 220/10; C08F 220/58; H01B 1/00
(52) U.S. Cl. ...................... 526/230.5; 526/227; 526/310; 252/500; 429/192
(58) Field of Search .............................. 526/230.5, 227, 526/310; 252/500; 429/192

(56) References Cited

U.S. PATENT DOCUMENTS

| | | | |
|---|---|---|---|
| 4,845,174 | * | 7/1989 | Amano et al. .................... 526/62 |
| 4,908,283 | * | 3/1990 | Takahashi et al. ................ 429/192 |
| 5,326,657 | * | 7/1994 | Suga et al. ...................... 429/192 |
| 5,369,197 | * | 11/1994 | Torenbeek et al. ................ 526/227 |
| 5,548,046 | * | 8/1996 | Sanchez ......................... 526/230.5 |
| 5,580,682 | * | 12/1996 | Chaloner-Gill ................... 252/62.2 |
| 5,597,661 | * | 1/1997 | Takeuchi et al. ................. 252/500 |
| 5,597,662 | * | 1/1997 | Isaacson et al. ................. 429/192 |
| 6,096,456 | * | 8/2000 | Takeuchi et al. ................. 429/249 |

FOREIGN PATENT DOCUMENTS

| | | |
|---|---|---|
| 4253771 | 9/1992 | (JP) . |
| 6187822 | 7/1994 | (JP) . |
| 6203841 | 7/1994 | (JP) . |
| 9073907 | 3/1997 | (JP) . |

* cited by examiner

*Primary Examiner*—Tae H. Yoon
(74) *Attorney, Agent, or Firm*—Sughrue, Mion, Zinn, Macpeak & Seas, PLLC

(57) ABSTRACT

Disclosed are (1) a thermopolymerizable composition containing a thermopolymerizable compound containing a (meth)acrylate having a moiety including oxyalkylene, fluorocarbon, oxyfluorocarbon and/or carbonate in the molecule, at least one electrolyte, and a polymerization initiator which is an organic peroxide containing no benzene ring, (2) a solid electrolyte obtained by thermally curing the composition, and (3) a primary battery, a secondary battery and electric double layer capacitor including the solid electrolyte, as well as a production method thereof. The polymer solid electrolyte obtained from the thermopolymerizable composition has high ion conductivity and good stability and the primary battery and secondary battery produced using the polymer solid electrolyte are operable at high capacity and high current, has a long-term service life and high reliability, and can be produced at low costs. Further the electric double layer capacitor is high in output voltage, and outputs a large amount of current, has high working ability, has a long-term service life and high reliability, and can be produced at low costs.

8 Claims, 2 Drawing Sheets

THERMOPOLYMERIZABLE COMPOSITION AND USE THEREOF

This invention claims benefit of a convention priority based on provisional application No. 60/064,731 filed Nov. 6, 1997.

FIELD OF THE INVENTION

The present invention relates to a thermopolymerizable composition for obtaining a highly ion-conductive solid polymer electrolyte, a solid polymer electrolyte obtained by polymerizing the thermopolymerizable composition and a production method thereof, and a battery or electric double layer capacitor using the solid polymer electrolyte and a production method thereof.

BACKGROUND OF THE INVENTION

In the trend toward downsizing and entire solidification in the field of ionics, demands are increasing for the practical use of an entire solid primary battery, secondary battery or electric double layer capacitor using a solid electrolyte as a new ion conductor which can substitute for the conventional electrolyte solution.

More specifically, batteries with a conventional electrolyte solution readily undergo the occurrence of liquid leakage or elution of the electrode material outside the battery and have a problem in the long-term reliability. Flexible sheet batteries which are hoped for in recent years also have a problem in that when an electrolyte solution is used, the internal impedance elevates or internal short circuit occurs due to the localization of electrolyte solution within the battery container or to the exhaustion of liquid.

Recently, electric double layer capacitors using a carbon material having a large specific surface area as the polarizable electrodes and placing an ion conductive solution therebetween are used in many cases as a power source for memory backup. However, such an electrolytic double layer capacitor also has a problem in the long-term use or reliability because when it is used for a long period of time or when a high voltage is applied, liquid leakage outside the capacitor readily occurs. On the other hand, electric double layer capacitors using a conventional inorganic ion conductive material further have a problem in that the decomposition voltage of the ion conductive material is low and, hence, the output voltage is low.

Batteries and electric double layer capacitors using a solid polymer electrolyte are free of problems such as liquid leakage or elution of the electrode material and can be processed into various shapes or easily sealed. They are also easy to be more reduced in the thickness.

Further, it is reported that in the electric double layer capacitor using a polyphosphazene-based organic polymer as the main component of the ion conductive material, the output voltage elevates as compared with those using an inorganic ion conductive material (see, for example, JP-A-4-253771 (the term "JP-A" as used herein means an "unexamined published Japanese patent application")).

Although solid polymer electrolytes under study in general are improved in the ion conductivity up to approximately from $10^{-4}$ to $10^{-5}$ S/cm at room temperature, this still stays in a level by two figures lower than that of solution-based ion conductive materials. The same applies to solid polymer electrolytes having introduced thereinto an oligooxyethylene chain, which are given much attention in recent years (see, for example, JP-A-4-211412 corresponding to U.S. Pat. No. 5,194,490). Further, there is a problem in that at low temperatures of 0° C. or less, the ion conductivity generally lowers to an extreme extent.

For installing a solid electrolyte into a battery or electric double layer capacitor, a so-called cast method have been used, where a solid electrolyte solution is coated and spread on a substrate such as an electrode and then the solvent is evaporated and removed. However, this technique is disadvantageous in that the working operation is complicated and adhesion to the electrode is unsatisfactory. There have been proposed a method of using a polymer gel electrolyte and a method of using a cross-linked solid polymer electrolyte impregnated with an electrolyte solution (see, for example, U.S. Pat. No. 4,792,504). However, when a large amount of electrolyte solution is contained in order to obtain a satisfactory ion conductivity, the curability or film forming property is deteriorated and the film strength is insufficiently high. Further, due to the fluidity imparted to it, the electrolyte cannot be treated as a complete solid and when it is applied to an electric double layer capacitor or battery, short circuit readily occurs and there arises a problem in the sealing property similarly to the solution-based ion conductive material.

Accordingly, there has been made investigation on a curing method in which an electrolyte and a polymerizable compound are used as the main components of the solid polymer electrolyte and these are loaded in a structural body of a battery or capacitor in the liquid or gel form and then cured to effect compounding.

As such a curing method of a polymerizable composition, there has hitherto been aggressively investigated for development of a curing method using an actinic radiation, and in particular, study is being made of solid polymer electrolytes to be prepared using an ultraviolet polymerization initiator, which is economically advantageous. However, when use is made of exposure to a radiation, it is difficult, due to the construction of the battery, to simultaneously compound and integrate the respective elements of the battery, i.e., a positive electrode, a negative electrode and/or a separator, as well as a polymerizable composition for the solid electrolyte. Particularly, in batteries of the type in which a positive electrode, a solid electrolyte and a negative electrode are laminated or wound, the elements are each not light transmissive and are difficult to be integrated. In order to prevent curing failure due to the transmission incapability of actinic radiation, it may be considered to compound the elements, i.e., the positive electrode and the negative electrode, and the polymerizable composition for solid electrolyte separately and then laminate or otherwise integrate them. However, problems occur in that the actinic radiation is shielded by the electrode material and the polymerizable composition inside the electrode is insufficiently cured so that the polymerization proceeds unevenly in the depth direction of the electrode or in that when a separator is interposed which is used in compensating for the mechanical strength or inter-electrode gap, uniform curing across and to the backside of the separator is difficult to attain. A further problem is involved in that the polymerization is vulnerable to inhibition by oxygen contained in the atmosphere which the polymerizable composition contacts, thereby causing curing failure.

For this reason, a curing method by heat curing has also been proposed, in which the respective elements, i.e., the positive electrode, the negative electrode and/or the separator and the solid electrolyte can be compounded and integrated simultaneously with the curing, and the construction of the battery allows reduction in the internal impedance of the battery. This method gains an advantage over any other methods for batteries of the type in which a positive electrode, a solid electrolyte and a negative electrode are laminated or wound, that are difficult to make by a photo-curing method with an actinic radiation. However, the problems as described below would occur. That is, in the preparation of a polymerizable composition for solid polymer electrolytes using a thermopolymerization initiator, the initiator is in many cases selected depending on the desired curing temperature. Accordingly, when the electrolyte solution contains a low boiling point solvent, use of initiators which generate radicals at high temperatures is restricted so as to prevent changes in the composition of solution due to the evaporation of the solvent. Consequently, it is attempted to use a polymerization accelerator in combination so that curing can be performed at a temperature of from room temperature to a medium temperature. The polymerization accelerator (in many cases, a reducing agent) or decomposition products thereof, however, will deteriorate the current properties such as ion conductivity or the characteristics such as cycle life, of the solid polymer electrolyte. If curing is performed only by heating without using any polymerization accelerator, it takes a long time for the curing to be completed at low temperatures since the curing rate depends on the thermal decomposition rate of the thermopolymerization initiator.

It is a common technique to increase the amount of the polymerization initiator or radicals generated so as to efficiently perform curing. However, unreacted initiator or decomposition products thereof increase in quantity and adversely affect the current properties such as ion conductivity or electrochemical characteristics such as cycle life. Furthermore, when the upside and/or inside of the electrode is compounded with a solid electrolyte, depending on the kind of the polymerization initiator, a problem occurs in that a gaseous decomposition product is generated and due to the gas, the electrode material may come off from the collector or the electrode may expand, thereby causing changes in the battery shape, or the electrochemical properties may be adversely affected, for example, the surface resistance increases or the cycle properties are deteriorated.

Use of peroxydicarbonate as a thermopolymerization initiator has also been proposed to solve the problem of gas generation (see, for example, JP-A-6-203841). However, a thermopolymerizable composition capable of exhibiting excellent electrical conductivity even at a low temperature and providing a cured product having sufficiently high strength and flexibility is not yet known.

OBJECTS OF THE PRESENT INVENTION

An object of the present invention is to provide a thermopolymerizable composition which has excellent ion conductivity and curability at room temperature and at a low temperature and has sufficiently high strength, by combining a polymerization initiator having high thermopolymerization initiating ability with a polymerizable compound having good curability.

Another object of the present invention is to provide a solid polymer electrolyte having high ion conductivity and good stability, which contains a polymer having a cross-linked and/or side-chained group obtained from the above-described thermopolymerizable composition and an electrolyte.

Still another object of the present invention is to provide a primary battery or secondary battery using the above-described solid polymer electrolyte inside the battery, which can work at a high capacity and a high current, has a long life and excellent reliability and can be produced cheaply.

Yet another object of the present invention is to provide an electric double layer capacitor using the above-described solid polymer electrolyte inside the capacitor, which has a high output voltage, a high takeout current, good processability, a long life and excellent reliability and can be cheaply produced.

SUMMARY OF THE INVENTION

As a result of extensive investigations to solve the above-described problems, the present inventors have found that a thermopolymerizable composition having very high curability can be obtained by combining a polymerizable compound having a specific structure with a thermopolymerization initiator which is an organic peroxide and also verified that from this composition, a solid polymer electrolyte can be produced even in the inside of the electrode or in the inside of the material where the actinic radiation cannot reach, and a solid polymer electrolyte obtained is good contacting property with an electrode. The present invention has been accomplished based on these findings. Further, the present inventors have verified that when use is made, as the above-described polymerizable compound, of the solid polymer electrolyte capable of exhibiting excellent ion conductivity at room temperature and low temperatures obtained starting from a urethane (meth)acrylate compound, which has been previously proposed by the present applicant (JP-A-9-73907), further excellent ion conductivity can be realized even at room temperature and low temperatures. The present invention has been accomplished based on this finding.

More specifically, the present invention provides a thermopolymerizable composition, a solid polymer electrolyte obtained by polymerizing the thermopolymerizable composition and a production method thereof, as well as a battery and/or electric double layer capacitor using the solid polymer electrolyte and a production method thereof.

1) A thermopolymerizable composition comprising at least one thermopolymerizable compound having a polymerizable functional group which compound becomes a polymer having a cross-linked and/or side-chained structure upon polymerization, at least one electrolyte and at least one polymerization initiator, wherein the thermopolymerizable compound contains a compound having a polymerizable functional group, represented by the following formula (1) and/or formula (2):

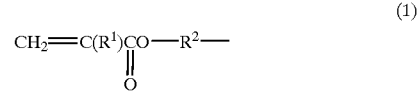

(1)

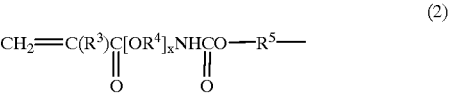

(2)

[wherein $R^1$ and $R^3$ independently represent hydrogen or an alkyl group, $R^2$ and $R^5$ independently represent a divalent group containing oxyalkylene, fluorocarbon, oxyfluorocarbon, and/or carbonate, $R^4$ represents a divalent group having 10 or less carbon atoms, $R^2$, $R^4$ and $R^5$ each may contain a hetero atom and may have any of linear, branched and cyclic structures, and x is 0 or an integer of from 1 to 10, provided that when a plurality of polymerizable functional groups represented by formula (1) or (2) are present in the same molecule, $R^1$, $R^2$, $R^3$, $R^4$, $R^5$ and x among the respective polymerizable functional groups may be the same or different], and the polymerization initiator is an organic peroxide represented by the following formula (3):

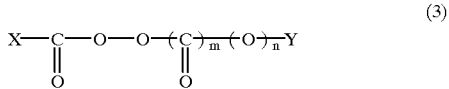
(3)

[wherein X represents an alkyl or alkoxy group which may have a substituent, Y represents an alkyl group which may have a substituent, X and Y each may have any of linear, branched and cyclic structures, and m and n are each 0 or 1, provided that a combination of (m,n)=(0,1) is excluded].

2) The thermopolymerizable composition as described in 1 above, wherein the organic peroxide is selected from diacylperoxides, peroxydicarbonates and peroxyesters containing no benzene ring.

3) The thermopolymerizable composition as described in 1 or 2 above, wherein the organic peroxide has an active oxygen amount of from 10 to 150 ppm based on the thermopolymerizable composition and the temperature necessary for obtaining a 10-hour half-life period of the active oxygen amount is from 40 to 70° C.

4) The thermopolymerizable composition as described in any one of 1 to 3 above, wherein the polymerizable composition further contains at least one non-aqueous organic solvent selected from carbonate esters, aliphatic esters, ethers, lactones, sulfoxides and amides, and the content of the organic solvent is 300 wt % or more based on the thermopolymerizable compound.

5) The thermopolymerizable composition as described in any one of 1 to 4 above, which contains at least one inorganic particle having an average diameter of from 0.005 to 100 μm.

6) The thermopolymerizable composition as described in any one of 1 to 5 above, wherein the electrolyte is at least one selected from alkali metal salts, quaternary ammonium salts, quaternary phosphonium salts, transition metal salts and protonic acids.

7) The thermopolymerizable composition as described in 6 above, wherein the at least one electrolyte is $LiPF_6$ and/or $LiBF_4$ and/or $LiAsF_6$ and/or $LiN(A-SO_2)_2$ where A is a perfluoroalkyl group having 1 to 10 carbon atoms.

8) A solid polymer electrolyte obtained by thermopolymerizing the thermopolymerizable composition described in any one of 1 to 7 above.

9) An electrode for a battery or an electric double layer capacitor, comprising the solid polymer electrolyte described in 8 above and an electrode-active material or a polarizable material.

10) A battery including the solid polymer electrolyte described in 8 above.

11) The battery as described in 10 above, wherein the negative electrode of the battery comprises lithium, a lithium alloy, a carbon material capable of occluding or releasing lithium ion, or an inorganic compound capable of occluding or releasing lithium ion.

12) The battery as described in 10 above, wherein the positive electrode of the battery comprises an electrically conductive polymer, a metal oxide, a metal sulfide and/or a carbon material.

13) An electric double layer capacitor using the solid polymer electrolyte described in 8 above.

14) A method for producing a battery, comprising injecting at least one thermopolymerizable composition described in any one of 1 to 7 above into a structural body for constructing a battery or placing it on a support, and then curing the thermopolymerizable composition by heating.

15) A method for producing an electric double layer capacitor, comprising injecting at least one thermopolymerizable composition described in any one of 1 to 7 above into a structural body for constituting an electric double layer capacitor or placing it on a support, and then curing the thermopolymerizable composition by heating.

DESCRIPTION OF THE PREFERRED EMBODIMENTS

[1] Thermopolymerizable Composition

Figure 1:
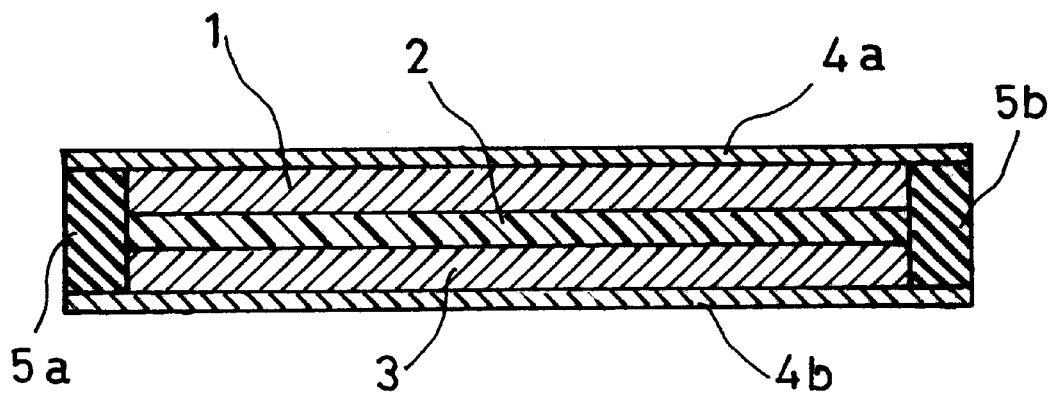
FIG. 1 is a schematic cross-sectional view showing a thin-type solid battery according to one embodiment of the present invention.

The thermopolymerizable composition of the present invention fundamentally comprises (a) a thermopolymerizable compound, (b) a polymerization initiator and (c) an electrolyte. The composition may further contain (d) a non-aqueous solvent and (e) an inorganic fine particle.

The thermopolymerizable composition of the present invention has a specific effect due to the combination of three components (a) to (c), in particular, the combination of (a) and (b). More specifically, in the thermopolymerizable compound having a polymerizable functional group represented by formula (1) and/or (2) which will be described below, the hetero atom accelerates the ionization of electrolyte salts and improves the ion conductivity of the solid electrolyte. Moreover, when this thermopolymerizable compound is combined with the polymerization initiator represented by formula (3), the reaction efficiently proceeds even if the active oxygen amount of the organic peroxide as the polymerization initiator based on the thermopolymerizable compound is very small and, therefore, curing can be performed even at room temperature or a medium temperature so that a very small number of double bonds can remain. The resulting cured product has excellent current characteristics and cycle characteristics and forms an electrochemically stable solid polymer electrolyte. More amazingly, when it contains a non-aqueous organic solvent, the composition exhibits good curability, high ion conductivity, excellent film forming property, and good film strength or electrochemical characteristics even when the amount of the organic solvent exceeds 300 wt % based on the polymerizable compound.

The constituent components of the thermopolymerizable composition of the present invention are described in detail below.

(a) Thermopolymerizable Compound
(i) The Structure of Thermopolymerizable Compound The thermopolymerizable compound for use in the present invention is a compound having a polymerizable functional group represented by the following general formula (1) and/or general formula (2):

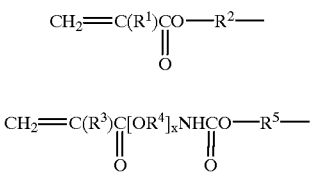

(1)

(2)

[wherein $R^1$ and $R^3$ independently represent hydrogen or an alkyl group, $R^2$ and $R^5$ independently represent a divalent group containing oxyalkylene, fluorocarbon, oxyfluorocarbon, and/or carbonate, $R^4$ represents a divalent group having 10 or less carbon atoms, $R^2$, $R^4$ and $R^5$ each may contain a hetero atom and may have any of linear, branched and cyclic structures, and x represents 0 or an integer of from 1 to 10, provided that when a plurality of polymerizable functional groups represented by formula (1) or (2) are present in the same molecule, $R^1$, $R^2$, $R^3$, $R^4$, $R^5$ and x among respective polymerizable functional groups are independent from each other and not necessary to be the same].

The polymerizable compound having a functional group represented by formula (1) or (2) comprises a (meth)acrylate structure and a segment containing oxyalkylene, fluorocarbon, oxyfluorocarbon, and/or carbonate. The (meth)acrylate structure forms a cross-linked or main chain on the polymerization reaction. The segment containing oxyalkylene, fluorocarbon, oxyfluorocarbon, and/or carbonate forms a cross-linked and/or side-chained structure after the polymerization. In this side-chained structure or the like, the hetero atom accelerates the ionization of the electrolyte salt to improve the ion conductivity of the solid electrolyte and further accelerates curing by the radical polymerization. As a result, a very small number of double bonds remain and complete curing results even with a small amount of the thermopolymerization initiator added.

In particular, it is preferred that the polymerizable functional group represented by formula (2) be included. When the thermopolymerizable compound has a polymerizable functional group represented by formula (2), the polymer obtained by polymerizing the compound contains a urethane group and is advantageous in that the dielectric constant is elevated and the solid polymer electrolyte formed therefrom has high ion conductivity. Further, the thermopolymerizable compound containing the structure of formula (2) is preferred since it has good polymerizability and when a thin film is formed therefrom, the film strength is advantageously great so that an increased amount of electrolyte solution can be contained therein.

While the oxyalkylene contained in $R^2$ of formula (1) or $R^5$ of formula (2) is not particularly limited, it is preferably an oligo- or greater polyoxyalkylene chain containing a structure represented by the following formula:

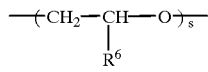

In this formula, $R^6$ is hydrogen or an alkyl side chain having 10 or less carbon atoms, and the alkyl side chain is preferably a methyl group. The repeating number, s, is an integer of from 1 to 1,000, preferably from 1 to 50. Different repeating units may contain different ($R^6$)s.

The fluorocarbon contained in $R^2$ of formula (1) or $R^5$ of formula (2) is not particularly limited. However, it is preferably a fluorocarbon comprising an alkylene chain having 20 or less carbon atoms of which hydrogens bonded to the carbon atoms are substituted by fluorine. The carbon chain skeleton may have any of linear, branched and cyclic structures.

The oxyfluorocarbon contained in $R^2$ of formula (1) or $R^5$ of formula (2) is not particularly limited. However, it is preferably an oligo- or greater polyoxyfluorocarbon chain containing a structure represented by the following formula:

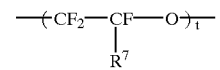

In this formula, $R^7$ is fluorine or a fluorocarbon side chain having 10 or less carbon atoms. The fluorocarbon side chain is preferably a perfluoromethyl group. The repeating number, t, is an integer of from 1 to 1,000, preferably from 1 to 50. Different repeating units may contain different ($R^7$)s.

The carbonate group contained in $R^2$ of formula (1) or $R^5$ of formula (2) is not limited particularly. However, it is preferably an oligo or greater polycarbonate chain containing a structure represented by the following formula:

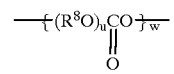

In this formula, $R^8$ is a linear, branched or cyclic divalent group having 1 to 10 carbon atoms which may contain one or more hetero atoms, u is an integer of from 1 to 10, and w is an integer of from 2 to 1,000.

The u in the formula above exceeding 10 is undesirable since the number of the carbonate groups in the polymer decreases to lower its dielectric constant, so that the electrolyte salts are difficult to dissolve. Preferably, u is 1 to 5.

Too large a number of carbon atoms in $R^8$ is undesirable since the number of the carbonate groups in the polymer decreases to lower its dielectric constant, so that the electrolyte salts are difficult to dissolve and since the hydrophobicity of the polymer increases to lower its compatibility with various polar solvents. Preferably, $R^8$ contains 1 to 6 carbon atoms, more preferably 1 to 4. The repeating number, w, is in the ranges of from 2 to 1,000, preferably from 3 to 100, and particularly from 5 to 50.

The remaining moiety of $R^2$ of formula (1) or $R^5$ of formula (2) may contain any of linear, branched and cyclic structures, and may contain one or more hetero atoms as long as the objects of the present invention are not impaired.

$R^4$ in formula (2) is preferably $(CH_2)_p(CH(CH_3))_q$ (wherein p and q each represents 0 or an integer of from 1 to 5, provided that when p=q=0, x=0). When x in $[OR^4]_x$ is 2 or more, $-CH_2-$ and $-CH(CH_3)-$ may be discontinued and irregularly arranged.

(ii) Production Method for Producing Thermopolymerizable Compound

The method for synthesizing the compound having a functional group represented by formula (1) is not particularly limited. However, when $R^2$ is an oxyalkylene group, it can be easily obtained by reacting an acid chloride with an oligooxyalkylenol having a hydroxyl group at the terminal.

For example, the compound having one functional group represented by formula (1) can be easily obtained by reacting an acid chloride with monoalkyl oligooxyalkylene glycol at a molar ratio of 1:1 according to the following reaction formula:

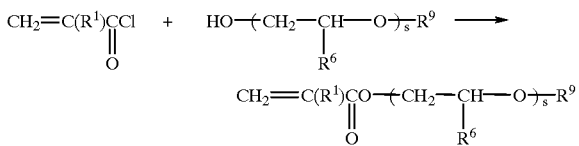

(wherein $R^1$ has the same meaning as in formula (1), $R^6$ and s have the same meanings as above, $R^9$ is a group which does not react with an acid chloride, for example, an alkyl group).

In the same way, the compound having two functional groups represented by formula (1) can be easily obtained by reacting an acid chloride with oligooxyalkylene glycol at a molar ratio of 2:1 according to the following reaction formula:

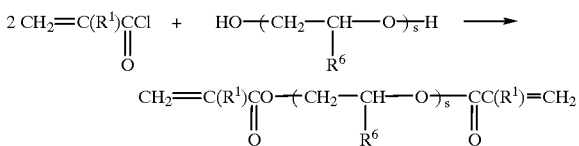

(wherein $R^1$, $R^6$ and s have the same meanings as above).

The same as above applies to compounds having three or more functional groups represented by formula (1), and a polymerizable compound having three, four, five or six functional groups represented by formula (1) within one molecule can be obtained by reacting an acid chloride with a triol such as glycerin, a tetraol such as pentaerythritol, a pentaol resulting from addition-polymerizing alkylene oxide to α-D-glucopyranose or a hexaol resulting from addition-polymerizing alkylene oxide to mannitol, at a ratio of 3:1, 4:1, 5:1 or 6:1, respectively.

The production method of the compound where $R^2$ has an oxyfluorocarbon is the same as above except for using an oxyfluorocarbon of such a structure that the hydrogens bonded to the carbon skeleton of the compound having a hydroxyl group are substituted by fluorine.

More specifically, a compound having one ethylenically unsaturated group, namely, a compound having one unit represented by formula (1) can be easily obtained, for example, by reacting an acid chloride with a monool such as 2,2,3,3,4,4,4-heptafluoro-1-butanol at a molar ratio of 1:1.

A compound having two ethylenically unsaturated groups, namely, a compound having two units represented by formula (1) or (2) can be easily obtained, for example, by reacting an acid chloride with a diol such as 2,2,3,3-tetrafluoro-1,4-butanediol at a molar ratio of 2:1.

The same as above applies to compounds having three or more units represented by formula (1).

The method for synthesizing a compound having an oxyalkylene group and a functional group represented by formula (2) for use in the solid polymer electrolyte of the present invention is not particularly limited. However, the compound can be easily obtained, for example, by reacting, in place of the above-described acid chloride, an isocyanate compound represented by the formula:

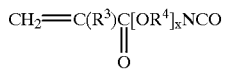

(wherein $R^3$, $R^4$ and x have the same meanings as in formula (2)) with an oligooxyalkylenol having a hydroxyl group at the terminal.

More specifically, a compound having one functional group represented by formula (2) can be easily obtained, for example, by reacting a methacryloyl isocyanate-based compound (hereinafter simply referred to as an MI) or acryloyl isocyanate-based compound (hereinafter simply referred to as an AI) with monoalkyl oligoalkylene glycol or the like at a molar ratio of 1:1 according to the following reaction formula:

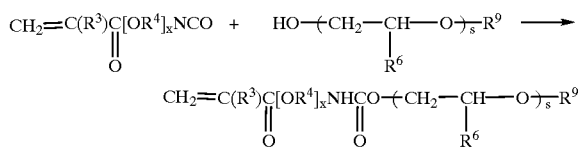

(wherein $R^3$, $R^4$, $R^6$, $R^9$, X and s have the same meanings as above).

The same as above applies to the compound having two or more functional groups represented by formula (2). For example, a compound having two functional groups represented by formula (2), a compound having three functional groups represented by formula (2), a compound having four functional groups represented by formula (2), a compound having five functional groups represented by formula (2) or a compound having six functional groups represented by formula (2) can be easily obtained by reacting an MI or AI with an oligoalkylene glycol at a molar ratio of 2:1, reacting an MI and/or AI with a triol resulting from addition-polymerizing alkylene oxide to a trihydric alcohol, at a molar ratio of 3:1, reacting an MI and/or AI with a tetraol resulting from addition-polymerizing an alkylene oxide to tetrahydric alcohol, at a molar ratio of 4:1, reacting an MI and/or AI with a pentaol resulting from addition-polymerizing an alkylene oxide to α-D-glucopyranose, at a molar ratio of 5:1, or reacting an MI and/or AI with hexaol resulting from addition-polymerizing alkylene oxide to mannitol, at a molar ratio of 6:1, respectively.

For introducing fluorocarbon or oxyfluorocarbon in place of oxyalkylene, the above-described reaction may be performed using a di- or greater polyhydric alcohol in which the hydrogen is substituted by fluorine. For example, when an MI or AI is reacted with a diol such as 2,2,3,3-tetrafluoro-1,4-butanediol at a molar ratio of 2:1 according to the following reaction formula, there can be obtained a thermopolymerizable compound containing 2 functional groups represented by formula (2) in the molecule which are bonded through perfluorocarbon.

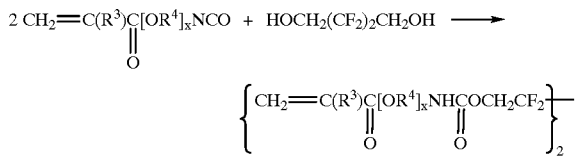

The same as above applies to compounds having three or more units represented by formula (2).

Specific examples of the polymerizable compound in which $R^2$ or $R^5$ is a moiety containing a carbonate group include the compounds represented by the following formula:

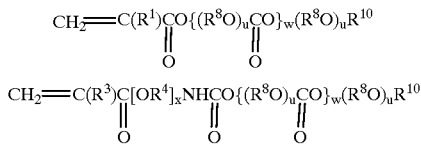

(wherein $R^{10}$ is a linear, branched and/or cyclic group which may contain one or more hetero atoms, and the other symbols have the same meanings as above).

The method for synthesizing the polymerizable compound which $R^2$ of formula (1) represents a moiety having a carbonate group is not particularly limited. However, such a compound can be obtained with ease, for example, by reacting an acid chloride with a poly- or oligocarbonate-ol having a hydroxyl group at the terminal.

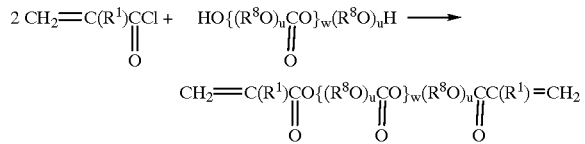

(wherein $R^1$, $R^8$, u and w have the same meanings as above).

The method for synthesizing the polymerizable compound which $R^5$ of formula (2) represents a moiety having a carbonate group is not particularly limited. However, such a compound can be obtained with ease, for example, by reacting an isocyanate compound represented by the formula:

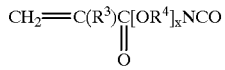

with a poly- or oligocarbonate-ol having a hydroxyl group at the terminal.

As a secific method, the compound having one functional group of formula (2) can be obtained with ease, for example, by reacting the above-described MI's or AI's with a monoalkyl poly- or oligocarbonate-ol in a molar ratio of 1:1 as in the following reaction scheme:

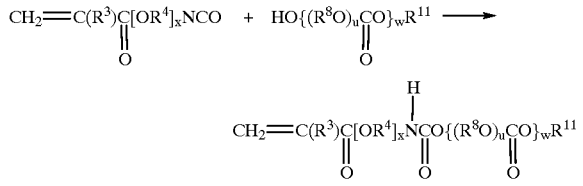

(wherein $R^{11}$ is a linear, branched and/or cyclic group which may contain one or more hetero atoms, and $R^3$, $R^4$, $R^8$, u, w and x have the same meanings as above).

Further, the polymerizable compound having two functional groups of formula (2) can be obtained with ease, for example, by reacting MI's or AI's with a poly- or oligocarbonate-ol in a molar ratio of 2:1 as in the following reaction scheme.

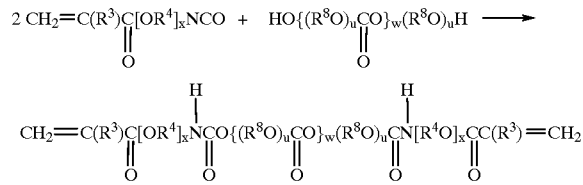

(wherein $R^3$, $R^4$, $R^8$, u, w and x have the same meanings as above).

Further, the compound having three fucntional groups of formula (2) can be obtained with ease, for example, by reacting MI's or AI's with a poly- or oligocarbonate-ol in a molar ratio of 3:1.

(iii) Use of Thermopolymerizable Compound

The thermopolymerizable compound for use in the present invention is polymerized by heating in the presence of a thermopolymerization initiator which will be described later, to form a solid polymer electrolyte. The compounds having a polymerizable functional groups represented by formula (1) or (2) may be used either individually or in combination of two or more thereof. Further, at least one of the compounds of formula (1) and/or (2) may be used in combination with one or more of other polymerizable compounds.

The polymer obtained by polymerizing a compound having only one functional group represented by formula (1) or (2) does not have a crosslinked structure and is deficient in the film strength and therefore, when a thin film is formed, short circuit may occur. Accordingly, it is preferred that the polymer be copolymerized and crosslinked with a polymerizable compound having two or more functional groups represented by formula (1) or (2) or used in combination with a polymer obtained from a polymerizable compound having two or more functional groups represented by formula (1) or (2). In the case when the polymer is used as a thin film, taking account of the film strength, it is preferred that the compound contain three or more functional groups represented by formula (1) or (2) in one molecule.

The other polymerizable compound copolymerizable with the compound having a polymerizable functional group represented by formula (1) and/or (2) is not particularly limited. Examples thereof include (meth)acrylic acid alkyl esters such as methyl methacrylate and n-butyl acrylate, various urethane acrylates, (meth)acrylamide-based compounds such as acrylamide, methacrylamide, N,N-dimethylacrylamide, N,N-dimethylmethacrylamide, vinylene carbonate, (meth)acryloyl carbonate, N-vinylpyrrolidone, acryloylmorpholine, methacryloylmorpholine and N,N-dimethylaminopropyl(meth)acrylamide, styrene-based compounds such as styrene and α-methylstyrene, N-vinylamide-based compounds such as N-vinylacetamide and N-vinylformamide, and alkyl vinyl ethers such as ethyl vinyl ether. Among these, preferred are (meth)acrylic acid ester and urethane (meth)acrylate, and more preferred in view of polymerizability is urethane (meth)acrylate.

(b) Thermopolymerization Initiator

The thermopolymerization initiator is roughly classified into two systems, one is a system which causes homolysis due to heat to generate radicals and another is a system which causes one-electron transfer reaction between two materials to generate radicals. The former includes a peroxide such as benzoyl peroxide and an azo compound such as azobisisobutyronitrile, and the latter includes an oxidation-reduction initiator.

In the present invention, an organic peroxide represented by formula (3) is used:

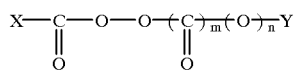
(3)

[wherein X represents an alkyl or alkoxy group which may have a substituent, Y represents an alkyl group which may have a substituent, X and Y each may have any of linear, branched and cyclic structures, provided that X and Y are independent from each other and not necessary to be the same, and m and n are each 0 or 1, provided that a combination of (m,n)=(0,1) is excluded].

An azo compound such as azobisdiphenylmethane, 2,2'-azobisisobutyronitrile and dimethyl-2,2 '-azobis(2-methylpropionate) generates gas accompanying radical generation and when a solid electrolyte is compounded at the upside and/or inside of the electrode, the gas disadvantageously causes falling-off of the electrode material from the collector or expansion of the electrode to thereby change the battery shape or adversely affects the current properties or electrochemical properties such as increase in the surface resistance or deterioration of cycle characteristics of the battery.

The peroxide having a benzene ring, for example, benzoin-based compounds such as benzoinisobutyl ether, acetophenone-based compounds such as diethoxyacetophenone, and benzophenone-based compounds such as benzophenone and methyl benzoylbenzoate, has a problem in the electrochemical stability because the thermal decomposition product thereof contains a phenyl group, and it is disadvantageous in that the battery formed is readily deteriorated in the cycle characteristics, the temperature necessary for reducing the active oxygen amount by half is generally high, deterioration or decomposition of electrolyte, solvent and polymer or volatilization of solvent readily occurs, and troubles in the electrochemical properties or in the production process are liable to take place.

On the other hand, the polymerization initiator represented by formula (3) is verified not to generate electrochemical problems such as reduction in the current properties or deterioration of cycle characteristics or not to cause peeling-off of the electrode from the collector or peeling-off of the solid polymer electrolyte from the electrode accompanying the gas generation, thereby increasing in the internal impedance.

Examples of the organic peroxide represented by formula (3) include diacylperoxide, peroxy dicarbonate and peroxyester, and specific examples thereof include 3,5,5-trimethylhexanoyl peroxide, lauroyl peroxide, stearoyl peroxide, octanoyl peroxide, di-n-propylperoxydicarbonate, diisopropylperoxydicarbonate, bis(4-t-butylcyclohexyl) peroxydicarbonate, di-2-ethoxyethylperoxydicarbonate, di-2-ethylhexylperoxydicarbonate, di-2-methoxybutylperoxydicarbonate, di(3-methyl-3-methoxybutyl)peroxydicarbonate, 1,1,3,3-tetramethylbutylperoxyneodecanate, 1-cyclohexyl-1-methylethylperoxyneodecanate, t-hexylperoxyneodecanate, t-butylperoxyneodecanate, t-hexylperoxypivalate, t-butylperoxypivalate, 1,1,3,3-tetramethylbutylperoxy-2-ethylhexanoate, 1-cyclohexyl-1-methylethylperoxy-2-ethylhexanoate and t-hexylperoxy-2-ethylhexanoate.

These organic peroxides may be used individually or in any combination. A combination of two or more thereof may also be used.

When the polymerizable compound and/or polymerizable composition is intended to be cured, curing is preferably performed at a temperature of from room temperature to a medium temperature in view of the problem in the heat stability of the solid polymer electrolyte or in the adhesion in compounding with various constituent materials such as electrode. Curing at a temperature of from room temperature to a medium temperature may be performed using an initiator and a reducing accelerator in combination or by decomposing an initiator only with heat. However, an initiator which cleaves by itself at room temperature or is first decomposed by heating and generates free radicals to exhibit activity is preferred. When curing is performed only with an aid of heating, selection of an optimal thermal decomposition rate of the initiator is only the matter to do and a combination of these initiators is also preferably used.

In the polymerizable composition of the present invention, the active oxygen amount defined by the following formula:

Active oxygen amount (wt %)=(amount of organic peroxide/amount of polymerizable composition)×(16×number of peroxide bonds/molecular weight of organic peroxide)

namely, the value obtained by dividing the atomic weight of active oxygen (—O—) present in the organic peroxide structure by the molecular weight of the organic peroxide and then multiplying the resulting value by the wt % of the organic peroxide occupying in the polymerizable composition, is from 1 to 1,000 ppm, preferably from 10 to 500 ppm, more preferably from 10 to 150 ppm. If the active oxygen amount is too small, the reaction does not proceed satisfactorily, whereas if the active oxygen amount is too large, a large number of terminates are formed due to the initiator and a low molecular weight polymer is liable to be produced, as result, a problem of deficient film strength is caused or the current properties or electrochemical properties are adversely affected, for example, the cycle property is deteriorated.

(c) Electrolyte

The kind of the electrolyte used in the present invention is not particularly limited and an electrolyte containing an ion which is intended to be a charge carrier may be used. However, electrolytes having a large dissociation constant in the solid polymer electrolyte are preferred and examples thereof include alkali metal salts of trifluoromethanesulfonic acid, such as $LiCF_3SO_3$, $NaCF_3SO_3$ and $KCF_3SO_3$, alkali metal salts of perfluoroalkanesulfonic imide, such as $LiN(CF_3SO_2)_2$ and $LiN(CF_3CF_2SO_2)_2$, alkali metal salts of hexafluorophosphoric acid such as $LiPF_6$, $NaPF_6$ and $KPF_6$, alkali metal salts of perchloric acid such as $LiClO_4$ and $NaClO_4$, tetrafluoroborates such as $LiBF_4$ and $NaBF_4$, and alkali metal salts such as LiSCN, $LiAsF_6$, LiI, NaI, $NaAsF_6$ and KI. Examples of the ammonium salt include quaternary ammonium salts of perchloric acid, such as tetraethylammonium perchlorate, quaternary ammonium salts of tetrafluoroboric acid, such as $(C_2H_5)_4NBF_4$, quaternary ammonium salts such as $(C_2H_5)_4NPF_6$, and quaternary phosphonium salts, such as $(CH_3)_4PBF_4$ and $(C_2H_5)_4PBF_4$. Among these electrolytes, $LiPF_6$, $LiBF_4$, $LiAsF_6$, alkali metal salts of perfluoroalkanesulfonic imide and quaternary ammonium salts are preferred.

The compounding ratio of the electrolyte to the polymer component [a polymer obtained by polymerizing a thermopolymerizable compound having a functional group represented by formula (1) or (2) and/or a polymer obtained by copolymerizing the compound as a copolymer component] in the solid polymer electrolyte of the present invention is preferably from 0.1 to 50 wt %, more preferably from 1 to 30 wt %, of the electrolyte based on the weight of the polymer. If the electrolyte used for compounding is present in a ratio exceeding 50 wt %, ion transfer is greatly inhibited, whereas if the ratio is less than 0.1 wt %, the absolute ion amount is insufficient and the ion conductivity is reduced.

(d) Non-Aqueous Organic Solvent

The solid polymer electrolyte of the present invention preferably contains a non-aqueous organic solvent as a solvent because the ion conductivity of the solid polymer electrolyte is further improved. The non-aqueous organic solvent which can be used is preferably a compound having good compatibility with the thermopolymerizable compound having a functional group represented by formula (1) and/or (2) for use in the solid polymer electrolyte of the present invention, and having a large dielectric constant, a boiling point of 70° C. or more and a broad electrochemically stable range.

Examples of the solvent include oligoethers such as triethylene glycol methyl ether and tetraethylene glycol dimethyl ether, carbonate esters such as ethylene carbonate, propylene carbonate, dimethyl carbonate, diethyl carbonate, methyl ethyl carbonate and vinylene carbonate, aliphatic esters such as methyl propionate and methyl formate, aromatic nitriles such as benzonitrile and trinitrile, amides such as dimethylformamide, sulfoxides such as dimethylsulfoxide, lactones such as γ-butyrolactone, sulfur compounds such as sulforane, N-methylpyrrolidone, N-vinylpyrrolidone, and phosphoric acid esters. Among these, carbonate esters, aliphatic esters and ethers are preferred, and carbonates are more preferred. These solvents may be used individually or they may be used as a mixed solvent of two or more thereof.

The larger the content of the non-aqueous organic solvent is, the more improved the ion conductivity of the solid polymer electrolyte formed is. Accordingly, the solvent content is preferably increased in general, however, if the content is too large, the curability, film-forming property or mechanical strength of the film is impaired. The polymerizable composition comprising a combination of a polymerizable composition containing a polymerizable functional group represented by formula (1) and/or formula (2) with an organic peroxide represented by formula (3) has characteristics such that even if the organic solvent content is increased, the curability is good and the film forming property or film mechanical strength is excellent, and therefore, the solvent can be added in an amount of 200 wt % or more based on the weight of the polymerizable compound used in the solid polymer electrolyte. In view of the current properties such as ion conductivity, the solvent is preferably added in an amount of 300 wt % or more.

(e) Inorganic Fine Particle

Although the constituent components of the solid polymer electrolyte produced by the present invention are described above in particular, other components may also be added as long as the object of the present invention is not impaired.

A composite electrolyte having added thereto various inorganic particles may be formed. By doing so, not only the strength and the film uniformity are improved but also due to small vacancy generated between the inorganic fine particle and the polymer, particularly when a solvent is added, free electrolyte solution flows into the vacancy to disperse within the composite electrolyte and thereby ion conductivity and mobility can be increased without impairing the effect of improving the strength. Further, the addition of inorganic fine particles have effects of increasing the viscosity of the polymerizable composition and preventing separation between the polymer and the solvent even when the compatibility therebetween is insufficient.

As the inorganic fine particle used, an electron non-conducting and electrochemically stable, preferably ion conductive, inorganic fine particle is selected. Specific examples thereof include ion conductive or electrically non-conducting ceramic-made fine particles such as α-, β- or γ-alumina and silica.

In view of improvement in the strength of the composite polymer electrolyte and increase in the amount of holding electrolyte solution, the inorganic fine particle preferably has a secondary particle structure resulting from agglomeration of primary particles. Specific examples of the inorganic fine particle having this structure include silica ultrafine particle such as Aerosil (produced by Nippon Aerosil KK) and alumina ultrafine particle. In view of stability and compounding efficiency, alumina ultrafine particle is preferred.

For the purpose of increasing the amount of holding electrolyte-containing solution in the electrolyte and thereby elevating the ion conductivity and mobility, the filler preferably has a specific surface area as large as possible and the specific surface area by the BET method is preferably 5 $m^2/g$ or more, more preferably 50 $m^2/g$ or more.

The inorganic fine particle is not particularly limited on the size as long as it can be mixed with the polymerizable composition, however, the size as average particle diameter is preferably from 0.01 to 100 $\mu$m, more preferably from 0.01 to 20 $\mu$m.

With respect to the shape of the inorganic fine particle, various shapes may be used, such as spherical form, egg form, cubic form, rectangular parallelopiped form, cylindrical form and bar form.

If the amount of inorganic fine particles added is too large, there arises problems that the strength or ion conductivity of the composite electrolyte is reduced or film formation is difficult to attain. Accordingly, the amount of the inorganic fine particle added is preferably 50 wt % or less, more preferably from 0.1 to 30 wt %, -based on the composite electrolyte.

(f) Order of Compounding

In manufacturing a thermopolymerizable composition of the present invention, the order of adding the thermopolymerization initiator is not particularly limited, however, for example, the following methods are preferred.

The thermopolymerization initiator represented by formula (3) may be added wholly or partially to any of the polymerizable compound and/or the solvent and/or the electrolyte solution and/or the polymerizable composition prepared therefrom, however, in view of the solubility, it is preferably added to the electrolyte solution and/or the polymerizable composition.

In the case when a radical polymerization retardant is used, it may be added to any of the polymerizable compound and/or the solvent and/or the electrolyte solution and/or the polymerizable composition prepared therefrom, however, in view of the stability, it is preferably added to the polymerizable compound.

[2] Solid Polymer Electrolyte and Production Process Thereof (Polymerization of Thermopolymerizable Composition)

A solid polymer electrolyte can be obtained by heating the above-described thermopolymerizable composition.

Preferred curing conditions of the thermopolymerizable composition may be set by selecting the thermopolymerization initiator according to the desired molding temperature, the kind and curability of the polymerizable compound, and the boiling point of the solvent, taking in consideration the temperature necessary for obtaining a half-life period of the active oxygen amount of the initiator being reduced to a half as a reference for the determination. The curing temperature and the curing rate may be determined by referring to the half-life period and activation energy of the thermopolymerization initiator. For example, in terms of the temperature required for reaching a 10 hour half-life period, a temperature of from room temperature to 100° C. is used, and from 40 to 70° C. is preferred.

Further, two or more thermopolymerization initiators different in the active oxygen amount, activation energy and half-life period may be freely selected and used in combination and for obtaining the object of the present invention, the initiator most suitable as a polymer ion conductor for the curing reaction and the curing conditions are preferably selected based on these indices.

When the thermopolymerization initiator represented by formula (3) was combined with an ion conductive solid polymer electrolyte (JP-A-6-187822) using a composite comprising a polymer polymerized from a polymerizable composition represented by formula (1) and/or (2), particularly, a (meth)acrylate monomer mixture containing an oxyalkylene group having a urethane bond represented by formula (2), and an electrolyte, curing occurred after heating at 60° C. for 15 minutes. The ion conductivity was high and $10^{-4}$ S/cm (at room temperature) even if a solvent was not added and it was found that when a solvent was further added, the ion conductivity was improved to $10^{-3}$ S/cm or more even at room temperature or a temperature lower than that. Moreover, when the cured product was applied to a battery or electric double layer capacitor, radicals were generated by heating from the polymerization initiator previously added to the system, to cure the thermopolymerizable composition, as a result, entire solidification of the solid polymer electrolyte could be realized.

The solid polymer electrolyte of the present invention may be compounded, for example, with various porous polymer films and used as a composite electrolyte, whereby improvement in the strength, film uniformity or prevention of inter-electrode short circuit can be attained. However, depending on the kind of the polymer used, the shape of film or the compounding ratio, the electrolyte film as a separator after absorption of the electrolyte solution is reduced in the ion conductivity or deteriorated in the stability. Accordingly, those must be selected appropriately. Examples of the film which can be used include network polyolefin sheet such as polypropylene non-woven fabric or polyethylene-made net, and examples of the separator which can be used include woven or non-woven fabric such as polyethylene and polypropylene, non-woven fabric such as glass fiber and ceramic fiber, a solid polymer electrolyte film, and a composite form thereof. The solid polymer electrolyte film and/or a composite form thereof are preferred as a separator because of their good adhesion and contacting property with the solid polymer electrolyte of the present invention.

The use embodiment of the solid polymer electrolyte of the present invention is described in greater detail below by referring to a battery and an electric double layer capacitor.

[3] Battery and Production Method Thereof

FIG. 1 is a schematic cross-sectional view showing a thin film battery as the battery according to one example of the present invention. In the Figure, 1 is a positive electrode, 2 is a solid polymer electrolyte, 3 is a negative electrode, 4a, 4b are each a collector and 5a, 5b are each an insulating resin sealant.

In the construction of the battery of the present invention, there can be obtained an electrode-active material (positive electrode-active material) having a high oxidation-reduction potential, such as a metal oxide, a metal sulfide, an electrically conductive polymer or a carbon material, is preferably used as the positive electrode 1 because a high-voltage high-capacity battery. Among these electrode-active materials, from the standpoint that high filling density and high volume capacity density can be attained, metal oxides such as cobalt oxide, manganese oxide, vanadium oxide, nickel oxide and molybdenum oxide, and metal sulfides such as molybdenum sulfide, titanium sulfide and vanadium sulfide, are preferred, and in view of high capacity and high voltage, manganese oxide, nickel oxide and cobalt oxide are more preferred.

In this case, the method for producing the metal oxide or metal sulfide is not particularly limited and these may be produced by a general electrolytic or heating method as described, for example, in *Denki Kagaku (Electrochemistry)*, Vol. 22, page 574 (1954). In the case when these are used in a lithium battery as an electrode-active material, an Li element in the form of $Li_xCoO_2$ or $Li_xMnO_2$ is preferably intercalated (compounded) into the metal oxide or metal sulfide at the production of the battery. The method for intercalating the Li element is not particularly limited and, for example, a method of electrochemically intercalating the Li ion or a method of mixing a salt such as $Li_2CO_3$ with a metal oxide and heat-treating the mixture as described in U.S. Pat. No. 4,357,215 may be used.

From the standpoint that a flexible and thin film can be easily formed, an electrically conductive polymer is preferred. Examples of the electrically conductive polymer include polyaniline, polyacetylene and derivatives thereof, polyparaphenylene and derivatives thereof, polypyrrole and derivatives thereof, polythienylene and derivatives thereof, polypyridinediyl and derivatives thereof, polyisothianaphthenylene and derivatives thereof, polyfurylene and derivatives thereof, polyselenophene and derivatives thereof, and polyarylene vinylene and derivatives thereof such as polyparaphenylene vinylene, polythienylene vinylene, polyfurylene vinylene, polynaphthenylene vinylene, polyselenophene vinylene and polypyridinediyl vinylene. Among these, a polymer of an aniline derivative soluble in an organic solvent is preferred.

As the negative electrode-active material used for the negative electrode 3 of the battery of the present invention, those having a low oxidation-reduction potential using the above-described alkali metal ion such as alkali metal, alkali metal alloy, carbon material, metal oxide or metal chalcogenide, as a carrier are preferably used because a high-voltage high-capacity battery can be obtained. Among these negative electrode-active materials, lithium metal and lithium alloys such as lithium/aluminum metal, lithium/lead alloy, lithium/antimony alloy are particularly preferred because of the lowest oxidation-reduction potential. Carbon materials are also preferred in the point that after occluding lithium ion, they exhibit a low oxidation-reduction potential and moreover, they are stable and safe. Examples of the material capable of occluding and releasing lithium ion include inorganic compounds such as tin oxide, natural graphite, artificial graphite, vaporphase graphite, petroleum coke, coal coke, pitch-based carbon, polyacene and furalenes such as C60 and C70.

For the collectors 4a, 4b, it is preferred to use those materials which are electroconductive and, electrochemically, have corrosion resistance and which have a specific surface area as large as possible. For example, various metals and sintered products thereof, electroconductive polymers, carbon sheet and the like.

One example of the method for producing the battery of the present invention is described.

The positive electrode 1 and the negative electrode 3 are placed in a structural body containing the collectors 4a, 4b for constructing a battery so as not to come into contact with each other with the intervention of the solid polymer electrolyte film 2 obtained from the thermopolymerizable composition of the present invention. Then, an electrolyte solution is injected and impregnated to obtain a battery containing a solid polymer electrolyte. When a thermopolymerizable composition is injected in place of the electrolyte solution, the polymerizable composition is cured by heating and completely solidified to obtain a battery containing a solid polymer electrolyte uniformly contacting with electrodes. Thereafter, the battery is sealed by the insulating resins 5a, 5b, such as polyolefin resin or epoxy resin.

A completely solidified battery can also be obtained by injecting and impregnating a polymerizable composition between electrodes fabricated so as not to come into contact with each other by interposing a separator between the positive electrode and the negative electrode, and curing the composition by heating.

A method of impregnating an electrolyte solution or polymerizable composition into the positive electrode and/or the negative electrode, coating the thermopolymerizable composition of the present invention on either one of the electrodes to have a uniform thickness, and then thermopolymerizing the composition by the above-described method to form a solid polymer electrolyte film having a uniform thickness on the electrode, may also be used. By laminating thereafter the other side electrode onto the solid polymer electrolyte layer, placing the laminate in a structural body for constructing a battery, and sealing it with an insulating resin such as polyolefin resin or epoxy resin, an objective battery can be obtained.

[4] Electric Double Layer Capacitor and Production Method Thereof

The electric double layer capacitor of the present invention is described below.

According to the present invention, an electric double layer capacitor having a high output voltage, a large takeout current, and excellent properties with respect to the workability, life and reliability can be obtained by using the above-described solid polymer electrolyte of the present invention.

Figure 2:
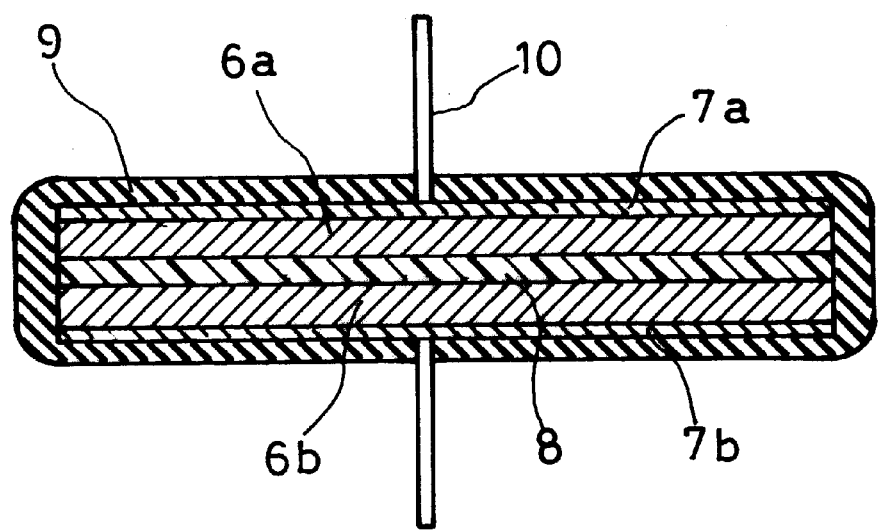
FIG. 2 is a schematic cross-sectional view showing a solid electric double layer capacitor according to one embodiment of the present invention.

FIG. 2 is a schematic cross-sectional view showing an electric double layer capacitor one example of the present invention. This example is a thin cell having a size of 1 cm×1 cm and a thickness of about 0.5 mm. 7a, 7b are each a collector and a pair of polarizable electrodes 6a, 6b are disposed in the inner side of the collector. Between the electrodes, a solid polymer electrolyte film 8 is disposed. 9 is an insulating resin sealant, and 10 is a lead wire.

The polarizable electrodes 6a, 6b are not particularly limited as long as they are each an electrode comprising a polarizable material such as carbon material and have a large specific surface area. Those having a larger specific surface area are preferred because the electric double layer can have a larger capacity. Examples thereof include carbon blacks such as furnace black, thermal black (including acetylene black) and channel black, activated carbon such as coco shell carbon, natural graphite, artificial graphite, so-called pyrolytic graphite produced by the vapor phase method, polyacene and C60, C70.

The collectors 7a, 7b are preferably formed from a material having electronic conduction, electrochemically corrosion resistant property and have a specific surface area as large as possible. Examples thereof include various metals and sintered body thereof, electron conductive polymers and carbon sheet.

With respect to the shape of the electric double layer capacitor, in addition to the sheet form shown in FIG. 2, a coin form and a cylinder form produced by rolling up the sheet laminate of polarizable electrodes and a solid polymer electrolyte into a cylinder form, placing the roll in a structural body having a cylindrical tubular form for constructing a capacitor, and sealing it, may also be used.

The kind of the electrolyte for use in the electric double layer capacitor of the present invention is not particularly limited and a compound containing an ion intended to serve as the charge carrier may be used, however, those containing an ion capable of exhibiting a large dissociation constant in the solid polymer electrolyte and facilitating the formation of an electric double layer with the polarizable electrodes are preferred. Examples of such compounds include quaternary ammonium salts such as $(CH_3)_4NBF_4$ and $(CH_3CH_2)_4NClO_4$, transition metal salts such as $AgClO_4$, quaternary phosphonium salts such as $(CH_3)_4PBF_4$, alkali metal salts such as $LiCF_3SO_3$, $LiPF_6$, $LiClO_4$, $LiI$, $LiBF_4$, $LiSCN$, $LiAsF_6$, $Li(CF_3SO_2)_2$, $NaCF_3SO_3$, $NaPF_6$, $NaClO_4$, $NaI$, $NaBF_4$, $NaAsF_6$, $KCF_3SO_3$, $KPF_6$ and $KI$, organic acids and salts thereof such as p-toluenesulfonic acid, and inorganic acids such as hydrochloric acid and sulfuric acid. Among these, from the standpoint that high output voltage can be taken out and the dissociation constant is large, quaternary ammonium salts, quaternary phosphonium salts and alkali metal salts are preferred. Among quaternary ammonium salts, those where the substituents on the nitrogens of the ammonium ion are different, such as $(CH_3CH_2)(CH_3CH_2CH_2CH_2)_3NBF_4$, are preferred because the solubility or dissociation constant in the solid polymer electrolyte is large.

One example of the method for producing the electric double layer capacitor of the present invention is described below.

Two polarizable electrodes 6a, 6b are placed in a structural body containing collectors 7a, 7b for constructing an electric double layer capacitor so as not to come into contact with each other with the intervention of the solid polymer electrolyte film 8 obtained from the thermopolymerizable composition of the present invention. Then, an electrolyte solution or polymerizable composition is injected thereinto and the body is sealed by an insulating resin 9 such as polyolefin resin or epoxy resin to obtain an objective electric double layer capacitor. In the case when a thermopolymerizable composition is injected, the composition is polymerized by heating and thereby an electric double layer capacitor completely solidified by the solid polymer electrolyte of the present invention can be obtained.

The structural body for constructing an electric double layer capacitor or the support may be a metal such as SUS, polypropylene, aluminum laminated heat fusing resin, polyimide, ethylene vinyl alcohol copolymer or a ceramic material such as electrically conductive or insulating glass, however, the present invention is not limited to those made by these materials. The shape may be a cylindrical form, a box form, a sheet form or any other form.

BEST MODE FOR CARRYING OUT THE INVENTION

The present invention is described in greater detail below by referring to representative Examples. However, these are only for the illustration and the present invention is by no means limited thereto.

EXAMPLE 1
Synthesis of Thermopolymerizable Compound (Compound 3)

According to the reaction formula shown below, a glycerin ester as Compound 1 and a methacrylate having an isocyanate group as Compound 2 were reacted, and through the following procedure, a thermopolymerizable compound (Compound 3) was obtained.

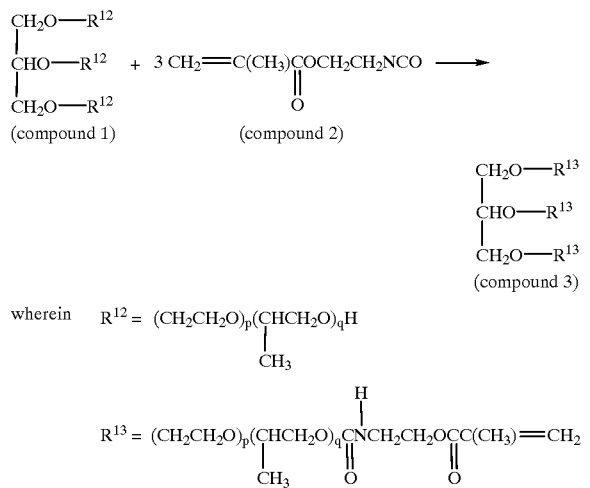

A mixture of 50.0 g of Compound 1 (KOH value: 34.0 mg/g, p/q=7/3) and 20 g of dimethyl carbonate was subjected to azeotropic treatment at 80° C. under reduced pressure of a vacuum degree of 3 mmHg and water was distilled off together with dimethyl carbonate to obtain 50 g of Compound 1 having a low water content. The water content of Compound 1 was determined by Karl Fischer's method and found to be 30 ppm. Then, Compound 1 (50 g) having a low water content and Compound 2 (4.6 g) were dissolved in thoroughly purified THF (100 ml) in a nitrogen atmosphere and thereto, 0.44 g of dibutyltin dilaurate was added. Thereafter, the mixture was reacted at 15° C. for about 25 hours to obtain a colorless viscous solution. From $^1$H-NMR and C-NMR, it is verified that Compound 1 and Compound 2 were reacted at a ratio of 1:3, and from the infrared absorption spectrum, absorption of the isocyanate group disappeared, a urethane bond was generated and Compound 3 was produced.

EXAMPLE 2
Preparation of Thermopolymerizable Composition

Compound 3 (1.0 g) was thoroughly mixed with 1.3 g of diethyl carbonate (DEC), 1.7 g of ethylene carbonate (EC), 0.50 g of $LiPF_6$ and 2.7 mg of lauroyl peroxide (PEROYL L, trade name, produced by Nippon Oils and Fats KK) as a thermopolymerization initiator in an argon atmosphere to obtain a polymerizable composition for a solid polymer electrolyte.

Figure 3:
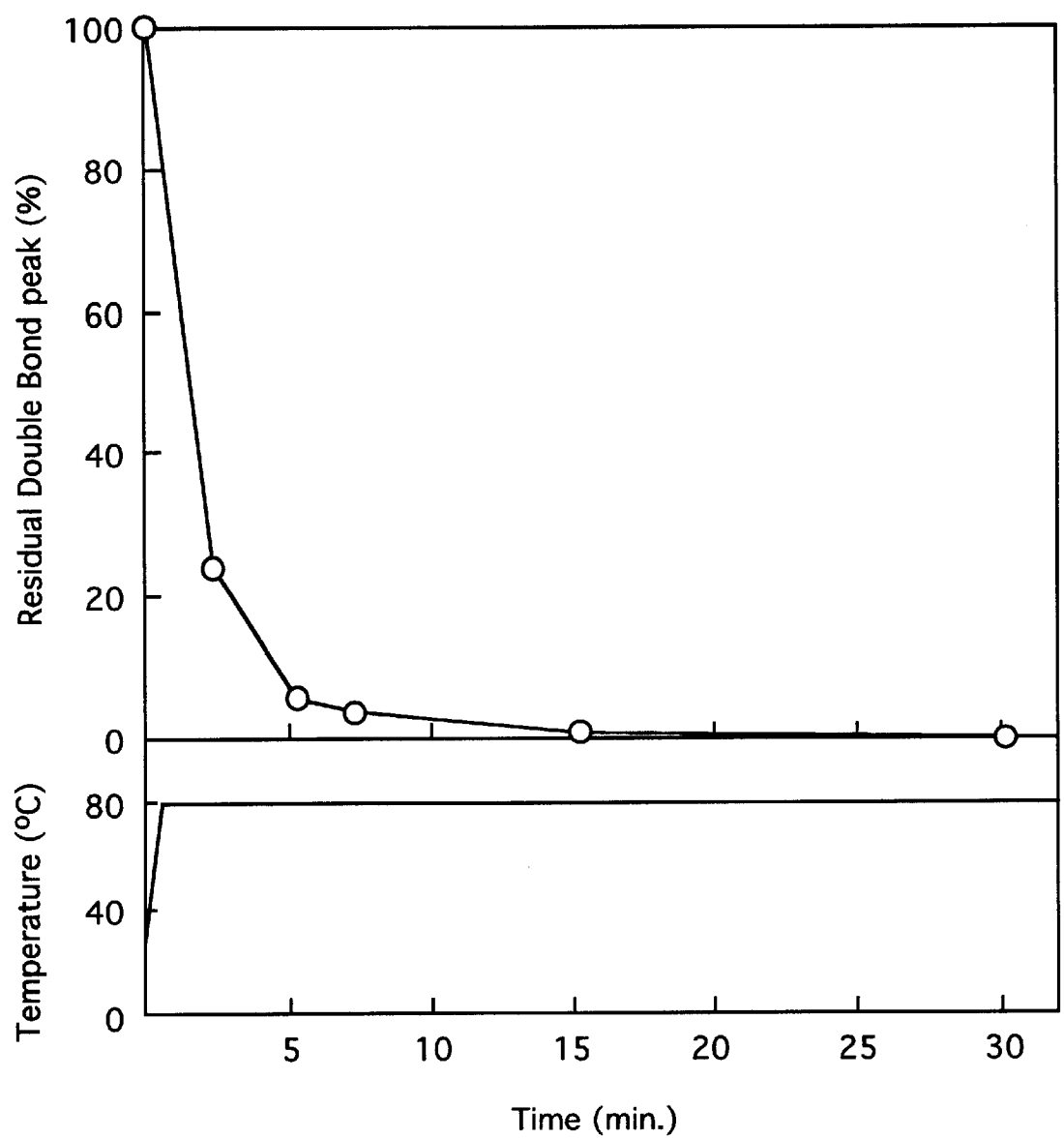
FIG. 3 is a graph showing the relationship between the heating and the residual double bond of the thermopolymerizable composition according to the present invention.

The composition obtained was interposed between two calcium fluoride sheets (diameter: 2 mm, thickness: 1 mm) to manufacture a cell for measurement of the infrared absorption spectrum. At this time, in order to secure the clearance, a polyimide film formwork having a thickness of 5 μm was used. Then, the cell manufactured was set in a hot stage (Hot Stage Model FP82, manufactured by Metler) and while heating the cell using a device FT-IR (BARROWER Model 3, manufactured by Nippon Bunko KK), the infrared spectrum was measured. From the peak area in the vicinity of 1,630 $cm^{-1}$ corresponding to the unsaturated bond, residual double bonds were quantitatively determined. A heating curve and a decreasing curve of residual double bonds are shown in FIG. 3. After heating at 80° C. for 10 minutes, the amount of residual double bonds was 0.1% or less which is the limit of determination.

EXAMPLE 3
Preparation of Solid Polymer Electrolyte Film A

Compound 3 (1.0 g) was thoroughly mixed with 1.3 g of diethyl carbonate (DEC), 1.7 g of ethylene carbonate (EC), 0.50 g of $LiPF_6$ and 4.5 mg of bis(4-t-butylcyclohexyl) peroxydicarbonate (PEROYL TCP, trade name, produced by Nippon Oils and Fats KK) as a thermopolymerization initiator in an argon atmosphere to obtain a polymerizable monomer solution for a solid polymer electrolyte.

Then, to the polymerizable monomer solution for a solid polymer electrolyte obtained, 0.27 g of aluminum oxide C (average secondary particle diameter: about 0.2 μm, produced by Nippon Aerosil KK, specific surface area: about 100 $m^2/g$) as inorganic fine particles was added in an argon atmosphere, and the solution was mixed while stirring for 5 minutes to obtain Polymerizable Composition A for a solid polymer electrolyte, containing milky inorganic fine particles.

Composition A obtained was coated on polypropylene (PP) film to have a thickness of 30 μm in an argon atmosphere, then another PP film was covered thereon, and this paired PP film was interposed between two 1.1 mm-thick glass plates. This paired glass plate was heated at 65° C. for 30 minutes and then the glass plate and PP film were peeled off. As a result, Solid Polymer Electrolyte Film A was obtained as a white blurred self-standing thin film having a thickness of about 30 μm.

The film obtained was determined on the ion conductivity at 25° C. and −10° C. by the impedance method and it was found to be $3\times10^{-3}$ and $1.0\times10^{-3}$ S/cm, respectively.

EXAMPLE 4
Preparation of Solid Polymer Electrolyte Film B

Compound 3 (1.0 g) was thoroughly mixed with 2.6 g of diethyl carbonate (DEC), 3.4 g of ethylene carbonate (EC), 1.0 g of $LiPF_6$ and 8.0 mg of bis(4-t-butylcyclohexyl) peroxydicarbonate (PEROYL TCP, trade name, produced by Nippon Oils and Fats KK) as a thermopolymerization initiator in an argon atmosphere to obtain a polymerizable monomer solution for a solid polymer electrolyte.

Then, to the polymerizable monomer solution for a solid polymer electrolyte obtained, 0.40 g of aluminum oxide C (average secondary particle diameter: about 0.2 μm, produced by Nippon Aerosil KK, specific surface area: about 100 $m^2/g$) as inorganic fine particles was added in an argon atmosphere, and the solution was mixed while stirring for 5 minutes to obtain Polymerizable Composition B for a solid polymer electrolyte, containing milky inorganic fine particles.

Composition B obtained was cured by heating at 65° C. for 30 minutes in the same manner as in Example 3, as a result, Solid Polymer Electrolyte Film B was obtained as a white blurred self-standing thin film having a thickness of about 30 μm.

The film obtained was determined on the ion conductivity at 25° C. and −10° C. by the impedance method and it was found to be $4.3\times10^{-3}$ and $1.5\times10^{-3}$ S/cm, respectively.

EXAMPLE 5
Production of Solid Polymer Electrolyte Film C

Compound 3 (1.0 g) was thoroughly mixed with 4.3 g of diethyl carbonate (DEC), 5.7 g of ethylene carbonate (EC), 1.5 g of LiPF$_6$ and 10 mg of 1,1,3,3-tetramethylbutylperoxyneodecanoate (PEROCTA ND, trade name, produced by Nippon Oils and Fats KK) in an argon atmosphere to obtain a polymerizable monomer solution for a solid polymer electrolyte.

Then, to the polymerizable monomer solution for a solid polymer electrolyte obtained, 0.55 g of aluminum oxide C (average secondary particle diameter: about 0.2 µm, produced by Nippon Aerosil KK, specific surface area: about 100 m$^2$/g) as inorganic fine particles was added in an argon atmosphere, and the solution was mixed while stirring for 5 minutes to obtain Polymerizable Composition C for a solid polymer electrolyte, containing milky inorganic fine particles.

Composition C obtained was cured by heating at 60° C. for 2 hours in the same manner as in Example 3, as a result, Solid Polymer Electrolyte Film C was obtained and the ion conductivity was 4.3×10$^{-3}$ and 1.5×10$^{-3}$ S/cm, respectively.

EXAMPLE 6
Production of Lithium Cobaltate Positive Electrode 11 g of Li$_2$CO$_3$ and 24 g of Co$_3$O$_4$ were thoroughly mixed and the mixture was heated in an oxygen atmosphere at 800° C. for 24 hours and pulverized to obtain LiCoO$_2$ powder. The LiCoO$_2$ powder obtained, acetylene black and polyvinylidene fluoride were mixed at a weight ratio of 8:1:1 and thereto, an excessive N-methylpyrrolidone solution was added to obtain a gel composition. This composition was coated and formed under pressure on an aluminum foil of about 50 µm to have a thickness of about 75 µm and thereby a lithium cobaltate positive electrode sheet was obtained. This sheet was cut into a 36 mm square and used as the positive electrode for a battery.

EXAMPLE 7
Production of Graphite Negative Electrode

To a 8.6:0.4:1.0 (by weight) mixture of MCMB graphite (produced by Osaka Gas), graphite fiber produced by a vapor phase method (produced by Showa Denko KK, average fiber diameter: 0.3 µm, average fiber length: 2.0 µm, heat-treated product at 2,700° C.) and polyvinylidene fluoride, an excessive N-methylpyrrolidone solution was added to obtain a gel composition. This composition was coated and formed under pressure on a copper foil of about 100 µm to have a thickness of about 85 µm and thereby a graphite negative electrode sheet was obtained. This sheet was cut into a 40 mm square and used as the negative electrode for a battery.

EXAMPLE 8
Production of Entire Solid Li Ion Secondary Battery

Within a glove box in an argon atmosphere, the sheet-like graphite negative electrode (40 mm square) produced in Example 7 was allowed to stand in Polymerizable Composition C prepared in Example 5 and impregnated with the composition. Thereafter, unnecessary Composition C on the negative electrode was wiped off by KIM wipe (trade name). On this negative electrode, Polymerizable Composition C prepared in Example 5 was coated using a 1-mil applicator to have a thickness of 25 µm. The resulting coating was covered with PP film and further with a 0.7 mm-thick glass plate and heated at 65° C. for 30 minutes on a hot plate with a thermostat to form a solid polymer electrolyte layer on the negative electrode.

Then, the PP film and the glass plate were peeled off and the resulting composite negative electrode was laminated with the lithium cobaltate positive electrode produced in Example 6 having previously impregnated therein Composition B prepared in Example 4. This laminate was placed in a bag made of a PP/Al/PET three-layer laminate (armor body) and heated at 65° C. for 30 minutes while pressurizing from both surfaces using 1.1 mm-thick glass plates to obtain a battery having compounded between electrodes thereof a solid polymer electrolyte.

This battery was charged and discharged at 25° C. or 10° C. at a working voltage of from 2.75 to 4.1 V and an electric current of 7 mA, as a result, the maximum discharge capacity was 29 mAh or 27 mAh, respectively. At this time, the electric current at the charging and discharging was monitored and other than the charge and discharge current, no reaction current originated from uncured product or initiator decomposition product was observed. Further, the battery was repeatedly charged and discharged at 25° C., a working voltage of from 2.75 to 4.1 V, a charge current of 7 mA and a discharge current of 35 mA but the capacity was not extremely reduced even after 300 cycles and it was 70% or more of the initial capacity.

EXAMPLE 9
Production of Entire Solid Li Ion Secondary Battery

Within a glove box in an argon atmosphere, the sheet-like graphite negative electrode produced in Example 7, the sheet-like lithium cobaltate positive electrode produced in Example 6 and a 38 mm-square polyolefin microporous film were allowed to stand in Polymerizable Composition C prepared in Example 5 and impregnated with the composition. Thereafter, the positive electrode and the negative electrode were laminated to each other with the intervention of the porous film. At this time, the lamination was performed such that the porous film slightly protruded from edges (4 sides) of the positive electrode. This laminate was placed in a bag made of a PP/Al/PET three-layer laminate (armor body) and heated at 60° C. for 2 hours while pressurizing from both surfaces using 1.1 mm-thick glass plates to obtain a battery having compounded between electrodes thereof a solid polymer electrolyte.

This battery was charged and discharged at 25° C. or 10° C. at a working voltage of from 2.75 to 4.1 V and an electric current of 7 mA, as a result, the maximum discharge capacity was 30 mAh or 28 mAh, respectively. At this time, the electric current at the charging and discharging was monitored and other than the charge and discharge current, no reaction current originated from uncured product or initiator decomposition product was observed. Further, the battery was repeatedly charged and discharged at 25° C., a working voltage of from 2.75 to 4.1 V, a charge current of 7 mA and a discharge current of 35 mA but the capacity was not extremely reduced even after 300 cycles and it was 70% or more of the initial capacity.

EXAMPLE 10
Production of Entire Solid Li Ion Secondary Battery

Within a glove box in an argon atmosphere, the sheet-like graphite negative electrode produced in Example 7 and the sheet-like lithium cobaltate positive electrode produced in Example 6 were allowed to stand in Polymerizable Composition C prepared in Example 5 and impregnated with the composition. Thereafter, the positive electrode and the negative electrode were laminated to each other with the intervention of Solid Polymer Electrolyte A produced in Example 3. At this time, the lamination was performed such that Solid Polymer Electrolyte Film A slightly protruded from edges (4 sides) of the positive electrode. This laminate was placed in a bag made of a PP/Al/PET three-layer laminate (armor body) and heated at 60° C. for 2 hours while pressurizing from both surfaces using 1.1 mm-thick glass plates to obtain an entire solid battery having compounded between electrodes thereof a solid polymer electrolyte film.

This battery was charged and discharged at 25° C. or 10° C. at a working voltage of from 2.75 to 4.1 V and an electric current of 7 mA, as a result, the maximum discharge capacity was 28 mAh or 26 mAh, respectively. At this time, the electric current at the charging and discharging was monitored and other than the charge and discharge current, no reaction current originated from uncured product or initiator decomposition product was observed. Further, the battery was repeatedly charged and discharged at 25° C., a working voltage of from 2.75 to 4.1 V, a charge current of 7 mA and a discharge current of 35 mA but the capacity was not extremely reduced even after 300 cycles and it was 70% or more of the initial capacity.

EXAMPLE 11
Production of Li Ion Secondary Battery

Within a glove box in an argon atmosphere, the sheet-like graphite negative electrode (40 mm square) produced in Example 7 was allowed to stand in a mixed electrolyte solution of ethylene carbonate containing 1 mol of $LiPF_6$ salt, and diethyl carbonate (1:1 by volume) and impregnated with the solution. Thereafter, unnecessary electrolyte solution on the negative electrode was wiped off by KIM wipe (trade name). On this negative electrode, Polymerizable Composition B produced in Example 4 was coated using a 1-mil applicator to have a thickness of 25 μm. The resulting coating was covered with PP film and further with a 0.7 mm-thick glass plate and heated at 65° C. for 30 minutes on a hot plate with a thermostat to form a solid polymer electrolyte layer on the negative electrode.

Then, the PP film and the glass plate were peeled off and the resulting composite negative electrode was laminated with the lithium cobaltate positive electrode produced in Example 6 having previously impregnated therein Composition C prepared in Example 5. This laminate was placed in a bag made of a PP/Al/PET three-layer laminate (armor body) and heated at 65° C. for 30 minutes while pressurizing from both surfaces using 1.1 mm-thick glass plates to obtain a battery having compounded between electrodes thereof a solid polymer electrolyte.

This battery was charged and discharged at 25° C. or 10° C. at a working voltage of from 2.75 to 4.1 V and an electric current of 7 mA, as a result, the maximum discharge capacity was 28 mAh or 26 mAh, respectively. At this time, the electric current at the charging and discharging was monitored and other than the charge and discharge current, no reaction current originated from uncured product or initiator decomposition product was observed. Further, the battery was repeatedly charged and discharged at 25° C., a working voltage of from 2.75 to 4.1 V, a charge current of 7 mA and a discharge current of 35 mA but the capacity was not extremely reduced even after 300 cycles and it was 70% or more of the initial capacity.

EXAMPLE 12
Production of Entire Solid Electric Double Layer Capacitor

Within a glove box in an argon atmosphere, two electrodes were prepared by impregnating an activated carbon electrode (14 mg) of 1 cm×1 cm with Composition C prepared in Example 5. Then, these two electrodes were laminated to each other with the intervention of Solid Polymer Electrolyte Film A produced in Example 3. Further, an Al thin foil collector (thickness: 50 μm, 1 cm×1 cm) connected to a lead wire was laminated on the electrode. After the capacitor edge part was sealed with epoxy resin, this was heated at 80° C. for 30 minutes. As a result, an electric double layer capacitor as shown in FIG. 2 was produced.

This capacitor was charged and discharged at a working voltage of from 0 to 2.0 V and a current of 0.2 mA, as a result, the maximum capacity was 430 mF. Under these conditions, the charging and discharging were repeated 50 times, but the capacity was scarcely changed.

Comparative Example 1
Production of Entire Solid Li Ion Secondary Battery Using Benzene Ring-Containing Compound Peroxide Solid Polymer Electrolyte D was prepared in the same manner as in Example 3 except for using 4.5 mg of benzoyl peroxide (NYPER BW, trade name, produced by Nippon Oils and Fats KK) as a thermopolymerization initiator in place of bis(4-t-butyl-cyclohexyl)peroxydicarbonate. Similarly to Example 10, within the glove box in an argon atmosphere, the sheet-like graphite negative electrode (prepared in Example 7) and the sheet-like lithium cobaltate positive electrode (prepared in Example 6) were allowed to stand in Polymerizable Composition D (a liquid before curing of Solid Electrolyte D) and impregnated with the composition. Thereafter, the positive electrode and the negative electrode were laminated to each other with the intervention of Solid Polymer Electrolyte D. At this time, the lamination was performed such that Solid Polymer Electrolyte Film D slightly protruded from edges (4 sides) of the positive electrode. This laminate was placed in a bag made of a PP/Al/PET three-layer laminate (armor body) and heated at 60° C. for 2 hours while pressurizing from both surfaces using 1.1 mm-thick glass plates to obtain an entire solid battery having compounded between electrodes thereof a solid polymer electrolyte film.

This battery was charged and discharged at 25° C. or 10° C. at a working voltage of from 2.75 to 4.1 V and an electric current of 7 mA, as a result, the maximum discharge capacity was 28 mAh or 26 mAh, respectively. At this time, the electric current at the charging and discharging was monitored and other than the charge and discharge current, slight reaction current originated from uncured product or initiator decomposition product was observed at the constant-voltage charging of 4.1 V. Further, the battery was repeatedly charged and discharged at 25° C., a working voltage of from 2.75 to 4.1 V, a charge current of 7 mA and a discharge current of 35 mA, then the capacity was reduced after 100 cycles and it was 50% or less of the initial capacity.

Comparative Example 2
Preparation of Solid Polymer Electrolyte Film E Containing no Oxyalkylene Structure A polymerizable monomer solution for a solid polymer electrolyte was obtained in the same manner as in Example 3 except for using 1.0 g of 1,2,3-tri(hydroxydodecyloxy) propane trimethacrylate (an acrylate compound containing no oxyalkylene structure)

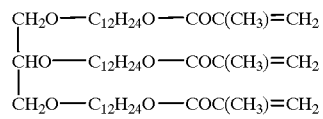

synthesized from glycerol and 1,12-dodecanediol in place of Compound 3.

Then, to the polymerizable monomer solution for a solid polymer electrolyte obtained, 0.27 g of aluminum oxide C (average secondary particle diameter: about 0.2 μm, produced by Nippon Aerosil KK, specific surface area: about 100 m²/g) as inorganic fine particles was added in an argon atmosphere, and the solution was mixed while stirring for 5 minutes to obtain Polymerizable Composition E for a solid polymer electrolyte, containing milky inorganic fine particles.

Composition E obtained was coated on polypropylene (PP) film to have a thickness of 30 $\mu$m in an argon atmosphere, then another PP film was covered thereon, and this paired PP film was interposed between two 1.1 mm-thick glass plates. This paired glass plate was heated at 65° C. for 30 minutes and then the glass plate and PP film were peeled off. As a result, Solid Polymer Electrolyte E was obtained as a white blurred self-standing thin film having a thickness of about 30 $\mu$m.

The film obtained was determined on the ion conductivity at 25° C. by the impedance method and it was found to be $1 \times 10^{-4}$ S/cm and be too ready to exude.

EXAMPLE 13

Synthesis of Compound 4

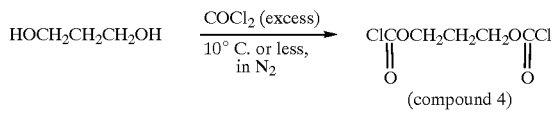

(compound 4)

According to the above-described reaction formula, by the common method, excess phosgene gas was blown into 1,3-propanediol at 10° C. or less under nitrogen atmosphere, and reaction was continued for about 5 hours to prepare compound 4. Identification was performed by GC-MS.

EXAMPLE 14

Oligomerization of Compound 4 (Synthesis of Compound 5)

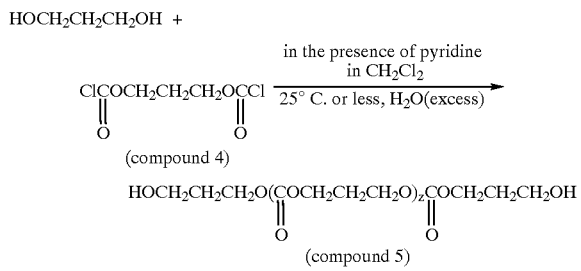

According to the above-described reaction formula, by the common method, Compound 4 prepared in Example 13 and 1,3-propanediol were reacted at 25° C. or less in the presence of pyridine in dichloromethane for about 6 hours and then excess water was added to hydroxylate the remaining chloroformate terminals to obtain oligocarbonate (Compound 5) having hydroxyl groups at both terminals thereof.

The resulting polymer had a weight average molecular weight (Mw) determined by GPC analysis and average repeating unit number, z, as described below.

Mw: about 1,200, z: about 10.

EXAMPLE 15

Synthesis of Polymerizable Compound 6

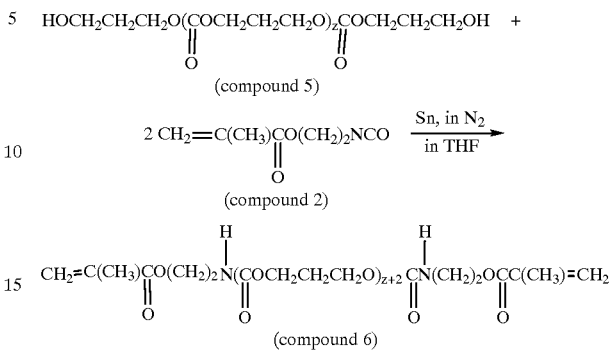

After dissolving 60.0 g of Compound 5 (average molecular weight 1,200) and 15.5 g of Compound 2 in highly purified THF (200 ml) in a nitrogen atmosphere, dibutyltin dilaurate (0.44 g) was added thereto. Thereafter, the reaction was continued at 25° C. for about 15 hours to obtain a colorless product. The results of $^1$H-NMR, IR and Elemental Analysis revealed that Compound 5 and Compound 2 reacted in a ratio of 1:2, and the isocyanate groups of Compound 2 disappeared and urethane bonding was generated, thus confirming that Compound 6 was produced.

EXAMPLE 16

Production of Solid Polymer Electrolyte Film F

Compound 6 (1.0 g) was thoroughly mixed with 4.3 g of diethyl carbonate (DEC), 5.7 g of ethylene carbonate (EC), 1.5 g of $LiPF_6$ and 10 mg of 1,1,3,3-tetramethylbutylperoxyneodecanoate (PEROCTA ND, trade name, produced by Nippon Oils and Fats KK) in an argon atmosphere to obtain a polymerizable monomer solution for a solid polymer electrolyte.

Then, the polymerizable monomer solution for a solid polymer electrolyte obtained was treated in the same manner as in Example 3 to obtain Polymerizable Composition F for a solid polymer electrolyte. Composition F obtained was cured by heating at 60° C. for 2 hours in the same manner as in Example 3 to obtain Solid Polymer Electrolyte Film F.

The film obtained was determined on the ion conductivity at 25° C. and −10° C. by the impedance method and it was found to be $5.3 \times 10^{-3}$ and $1.7 \times 10^{-3}$ S/cm, respectively.

EXAMPLE 17

Production of Entire Solid Li Ion Secondary Battery

Within a glove box in an argon atmosphere, the sheet-like graphite negative electrode produced in Example 7, the sheet-like lithium cobaltate positive electrode produced in Example 6, and 38 mm-square polyolefine microporous film were allowed to stand in Polymerizable Composition F prepared in Example 16 and impregnated with the composition. Thereafter, the positive electrode and the negative electrode were laminated to each other with the intervention of the porous film. At this time, the lamination was performed such that the porous film slightly protruded from edges (4 sides) of the positive electrode. This laminate was placed in a bag made of a PP/Al/PET three-layer laminate (armor body) and heated at 60° C. for 2 hours while pressurizing from both surfaces using 1.1 mm-thick glass plates to obtain an entire solid battery having compounded between electrodes thereof a solid polymer electrolyte film.

This battery was charged and discharged at 25° C. or 10° C. at a working voltage of from 2.75 to 4.1 V and an electric current of 7 mA, and as a result, the maximum discharge capacity was 33 mAh or 30 mAh, respectively. At this time, the electric current at the charging and discharging was monitored and other than the charge and discharge current, no reaction current originated from uncured product or initiator decomposition product was observed. Further, the battery was repeatedly charged and discharged at 25° C., a working voltage of from 2.75 to 4.1 V, a charge current of 7 mA and a discharge current of 35 mA but the capacity was not extremely reduced even after 300 cycles and it was 75% or more of the initial capacity.

EXAMPLE 18
Production of Entire Solid Electric Double Layer Capacitor

Within a glove box in an argon atmosphere, two electrodes were prepared by impregnating an activated carbon electrode (14 mg) of 1 cm×1 cm with Composition F prepared in Example 16. Then, these two electrodes were laminated to each other with the intervention of Solid Polymer Electrolyte Film F produced in Example 16. Further, an Al thin foil collector (thickness: 50 μm, 1 cm×1 cm) connected to a lead wire was laminated on the electrode. After the capacitor edge part was sealed with epoxy resin, this was heated at 80° C. for 30 minutes. As a result, an electric double layer capacitor as shown in FIG. 2 was produced.

This capacitor was charged and discharged at a working voltage of from 0 to 2.0 V and a current of 0.2 mA, as a result, the maximum capacity was 450 mF. Under these conditions, the charging and discharging were repeated 50 times, but the capacity was scarcely changed.

INDSUTRIAL APPLICABILITY

The thermopolymerizable composition of a solid polymer electrolyte of the present invention contains a thermopolymerization initiator having high stability with respect to the electrochemical characteristics such as current property and cycle property, and a specific polymerizable compound having very good polymerizability, accordingly, polymerization completely proceeds with a small amount of the initiator added even at a temperature of from room temperature to a medium temperature. Thus, this is a polymerizable composition not adversely affecting the stability of a battery or electric double layer capacitor and having excellent curability.

The solid polymer electrolyte of the present invention contains a polymer having a cross-linked and/or side-chained group obtained from the above-described thermopolymerizable composition and an electrolyte, and this is a solid polymer electrolyte having high ion conductivity and good stability.

The battery of the present invention is easy to be formed into a thin film because it uses the above-described solid polymer electrolyte and further, since the electrolyte can be easily compounded with each element such as a positive electrode and/or a negative electrode and/or a separator, the battery can work at a high capacity and a high current and has a long life and excellent reliability.

The battery of the present invention can work at a high capacity and high current as an entire solid-type and has good cycle property, excellent safety and superior reliability, accordingly, it can be used as a power source for electrical products including a main power source for portable appliances and a backup power source, or as a large-sized power source for electric cars or road leveling. Further, the battery can be easily formed into a thin film and therefore, it can be used also as a paper battery such as an identification card.

The electric double layer capacitor of the present invention uses the above-described solid polymer electrolyte and therefore, it has a high output voltage, a high takeout current, good processability, a long life and excellent reliability.

Further, the electric double layer capacitor of the present invention is an entire solid electric double layer capacitor which can work at a high voltage, a high capacity and a high current, and has good cycle property, superior safety and excellent reliability, as compared with conventional entire solid-type capacitors. Accordingly, it can be used not only as a backup power source but also in combination with a compact battery, can be used as a power source for various electrical products. Furthermore, the electric double layer capacitor of the present invention has excellent processability such as formation into a thin film and therefore, it can be utilized in uses other than those of conventional solid-type electric double layer capacitors.

What is claimed is:

1. A thermopolymerizable composition comprising at least one thermopolymerizable compound having a polymerizable functional group which compound becomes a polymer having a cross-linked and/or side-chained structure upon polymerization, at least one electrolyte, and at least one polymerization initiator, wherein said polymerizable functional group is represented by the following formula (1) and/or formula (2):

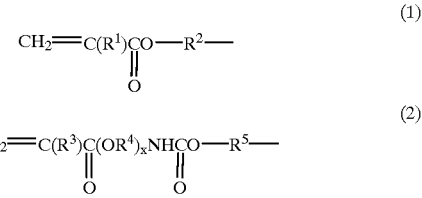

wherein $R^1$ and $R^3$ independently represent hydrogen or an alkyl group, $R^2$ independently represents a divalent group containing fluorocarbon, oxyfluorocarbon, and/or carbonate, $R^4$ represents a divalent group having 10 or less carbon atoms, $R^5$ independently represents a divalent group containing oxyalkylene, fluorocarbon, oxyfluorocarbon, and/or carbonate, $R^2$, $R^4$, and $R^5$ each may contain a hetero atom and may have any of linear, branched and cyclic structures, and x is 0 or an integer of from 1 to 10, provided that when a plurality of polymerizable functional groups represented by formula (1) or (2) are present in the same molecule, $R^1$, $R^2$, $R^3$, $R^4$, $R^5$, and x among the respective polymerizable functional groups may be the same or different, further wherein said polymerization initiator is an organic peroxide, which does not have a benzene ring, selected from the group consisting of 3,5,5-trimethylhexanoyl peroxide, stearoyl peroxide, octanoyl peroxide, 1,1,3, 3-tetramethylbutyl peroxyneodecanate, 1-cyclohexyl-1-methylethyl peroxyneodecanate, t-hexyl peroxyneodecanate, t-butyl peroxyneodecanate, t-hexyl peroxypivalate, 1,1,3,3-tetramethylbutyl peroxy-2-ethylhexanoate, 1-cyclohexyl-1-methylethyl peroxy-2-ethylhexanoate and t-hexyl peroxy-2-ethylhexanoate, and still further wherein said thermopolymerizable composition is accelerator-free.

2. The thermopolymerizable composition as claimed in claim 1, wherein said organic peroxide has an active oxygen amount of 1 to 1000 ppm based on the thermopolymerizable composition.

3. The thermopolymerizable composition as claimed in claim 2, wherein a 10-hour half-life period of the active oxygen amount of said organic peroxide is obtained at a temperature of 40 to 70° C.

4. The thermopolymerizable composition as claimed in claim 1, wherein said thermopolymerizable composition further contains at least one non-aqueous organic solvent selected from the group consisting of carbonate esters, aliphatic esters, ethers, lactones, sulfoxides, and amides, and the content of said organic solvent is 300 wt % or more based on the thermopolymerizable compound.

5. The thermopolymerizable composition as claimed in claim 1, which contains at least one inorganic particle having an average diameter of 0.005 to 100 μm.

6. The thermopolymerizable composition as claimed in claim 1, wherein said electrolyte is at least one selected from the group consisting of alkali metal salts, quaternary ammonium salts, quaternary phosphonium salts, transition metal salts, and protonic acids.

7. The thermopolymerizable composition as claimed in claim 6, wherein at least one electrolyte is $LiPF_6$ and/or $LiBF_4$ and/or $LiAsF_6$ and/or $LiN(A-SO_2)_2$ where A is a perfluoroalkyl group having 1 to 10 carbon atoms.

8. A solid polymer electrolyte obtained by thermopolymerizing the thermopolymerizable composition described in any one of claims 1–3 or 4–7.

* * * * *